(12) United States Patent
Nakazumi (10) Patent No.: US 12,115,100 B2
(45) Date of Patent: Oct. 15, 2024

(54) ENDOSCOPIC CANCER TREATMENT SYSTEM

(71) Applicant: AD ME TECH CO., LTD., Ehime (JP)

(72) Inventor: Shinichi Nakazumi, Ehime (JP)

(73) Assignee: AD ME TECH CO., LTD., Ehime (JP)

( * ) Notice: Subject to any disclaimer, the term of this patent is extended or adjusted under 35 U.S.C. 154(b) by 790 days.

(21) Appl. No.: 17/271,594

(22) PCT Filed: Aug. 29, 2019

(86) PCT No.: PCT/JP2019/033928
§ 371 (c)(1),
(2) Date: Nov. 5, 2021

(87) PCT Pub. No.: WO2020/045572
PCT Pub. Date: Mar. 5, 2020

(65) Prior Publication Data
US 2022/0062032 A1  Mar. 3, 2022

(30) Foreign Application Priority Data
Aug. 31, 2018  (JP) .................................. 2018-162983

(51) Int. Cl.
*A61B 8/12*  (2006.01)
*A61B 17/34*  (2006.01)
(Continued)

(52) U.S. Cl.
CPC ................. *A61F 7/12* (2013.01); *A61B 8/12* (2013.01); *A61B 17/3478* (2013.01);
(Continued)

(58) Field of Classification Search
CPC . A61B 8/12; A61B 17/3478; A61B 2017/003; A61B 2017/0034; A61F 7/12
See application file for complete search history.

(56) References Cited

U.S. PATENT DOCUMENTS 6,176,856 B1  1/2001  Jandak et al.
2004/0030369 A1*  2/2004  Kubota .................... A61N 5/06
                                                          607/89
(Continued)

FOREIGN PATENT DOCUMENTS

EP  1791483  6/2007
EP  2977032  1/2016
(Continued)

*Primary Examiner* — Baisakhi Roy
(74) *Attorney, Agent, or Firm* — David R. Stevens; Stevens Law Group (57) ABSTRACT

The purpose of the present invention is to provide an endoscopic cancer treatment system capable of heating and treating only cancer tissues at pinpoint more surely, when treating a cancer in visceral organs such as a pancreatic cancer. An endoscopic cancer treatment system for heating and treating cancer tissues to be a lesion, which is used in combination with an ultrasonic endoscope used in an endoscopic ultrasound-guided fine needle aspiration, comprising: a heating needle provided with a heater and a temperature detecting element at tip side; and a controller for controlling the heater to a predetermined temperature based on a temperature data detected by the temperature detecting element, wherein the heating needle is configured to be inserted through an instrument insertion channel provided in an inserting section of the ultrasonic endoscope to be able to protrude or retract from a tip opening provided at a tip side of the inserting section.

3 Claims, 7 Drawing Sheets

(51) Int. Cl.
  *A61F 7/12* (2006.01)
  *A61B 17/00* (2006.01)
  *A61F 7/00* (2006.01)

(52) U.S. Cl.
  CPC ............... *A61B 2017/0003* (2013.01); *A61B 2017/0034* (2013.01); *A61B 2017/00818* (2013.01); *A61F 2007/0071* (2013.01); *A61F 2007/126* (2013.01)

(56) References Cited

U.S. PATENT DOCUMENTS

| | | | | |
|---|---|---|---|---|
| 2004/0143252 A1* | 7/2004 | Hurst | ............... | A61B 18/1477 |
| | | | | 606/41 |
| 2005/0090818 A1* | 4/2005 | Pike | ............... | A61B 18/1492 |
| | | | | 606/41 |
| 2009/0163767 A1* | 6/2009 | Tsutaki | ............... | A61B 8/12 |
| | | | | 600/104 |
| 2009/0227866 A1* | 9/2009 | Nakazato | ............ | A61B 17/1114 |
| | | | | 128/898 |
| 2010/0049188 A1* | 2/2010 | Nelson | ............... | A61B 18/1492 |
| | | | | 606/34 |
| 2011/0118725 A1 | 5/2011 | Mayse et al. | | |
| 2011/0166563 A1* | 7/2011 | Cheng | ............... | A61B 18/082 |
| | | | | 606/30 |
| 2012/0078094 A1 | 3/2012 | Nishina | | |
| 2013/0211176 A1 | 8/2013 | Habib | | |
| 2013/0338477 A1* | 12/2013 | Glossop | ............. | A61B 10/0241 |
| | | | | 600/407 |
| 2014/0200568 A1* | 7/2014 | Sharma | ............... | A61B 5/1076 |
| | | | | 606/27 |
| 2015/0272654 A1 | 10/2015 | Esch et al. | | |
| 2018/0064415 A1* | 3/2018 | Zhai | ............... | A61N 7/02 |
| 2019/0201557 A1* | 7/2019 | Abo | ............... | A61K 49/0409 |
| 2021/0113286 A1* | 4/2021 | Oude-Vrielink | ....... | A61B 34/76 |

FOREIGN PATENT DOCUMENTS

| | | |
|---|---|---|
| JP | 2004290351 A | 10/2004 |
| JP | 2012024583 A | 2/2012 |
| JP | 2014008101 A | 1/2014 |
| JP | 2016101360 A | 6/2016 |
| JP | 2018118115 A | 8/2018 |
| KR | 20090131724 | 12/2009 |
| WO | 2009/137819 | 11/2009 |
| WO | 2014148289 A1 | 9/2014 |
| WO | 2017090165 A1 | 6/2017 |

\* cited by examiner

ENDOSCOPIC CANCER TREATMENT SYSTEM

BACKGROUND OF THE INVENTION

Field of the Invention

The present invention relates to an endoscopic cancer treatment system for treating a cancer tissue to be a lesion, in a visceral organ such as a pancreas by heating. The present application claims priority based on Japanese Patent Application No. 2018-162983 filed in Japan on Aug. 31, 2018, which is incorporated by reference herein.

Description of Related Art

It is understood that cancer cells will be killed at a temperature of about 42 degrees Celsius, so as one manner of cancer treatment method, a treatment to selectively heat a lesion where cancer tissues exist has been practiced conventionally. For example, in Patent Literature 1, a cancer treatment device comprising: a heating element in which a heating body made of a material generating heat by electromagnetic induction is adhered with a ligand which selectively bonds to cancer cells; and an inductive heating means for irradiating an electromagnetic wave to the heating element in a state that the heating element is bonded to an affected part composed of cancer cells of a body to be treated, is disclosed. The cancer treatment device is characterized to selectively heat and destroy cancer cells only by inductively heating the heating element.

In addition, in Patent Literature 2, as a curing device by killing and destroying a lesion such as cancer cells by directly heating the lesion, a thermotherapeutic device comprising: an injection section for injecting a metal lake solution to a lesion; and a heating section for directly heating the injected metal lake solution by a high-frequency current, wherein the metal lake solution is boiled by the heating section to kill the lesion such as cancer cells, is disclosed. In the thermotherapeutic device, the metal lake solution injected to the lesion is directly heated and boiled, so it is possible to kill the lesion surely by completely heating the lesion and its nearby areas.

Patent Literature 1: JP2004-290351 A
Patent Literature 2: JP2014-008101 A

SUMMARY OF THE INVENTION

However, when performing a cancer treatment by heating cancer tissues to be a lesion, it is necessary to heat only the cancer tissues to be the lesion surely to a desired temperature, and also, it is necessary to avoid heating healthy tissues other than the cancer tissues. Especially, among visceral organs to be a target of cancer treatment, different from a liver or the like, a pancreas does not have a cell regenerating function, so when performing a cancer treatment by heating, it is desired to treat by heating only the cancer tissues to be the lesion at pinpoint to a desired temperature, by avoiding to heat healthy tissues more surely.

The present invention is invented considering the above problems, and a purpose of the present invention is to provide a new and improved endoscopic cancer treatment system capable of heating and treating only cancer tissues at pinpoint more surely, when treating a cancer in visceral organs such as a pancreatic cancer.

One embodiment of the present invention is an endoscopic cancer treatment system for heating and treating cancer tissues to be a lesion, which is used in combination with an ultrasonic endoscope used in an endoscopic ultrasound-guided fine needle aspiration, comprising: a heating needle provided with a heater and a temperature detecting element at a tip side; and a controller for controlling the heater to a predetermined temperature based on a temperature data detected by the temperature detecting element, wherein the heating needle is configured to be inserted through an instrument insertion channel provided in an inserting section of the ultrasonic endoscope to be able to protrude or retract from a tip opening provided at a tip side of the inserting section.

According to one embodiment of the present invention, the cancer tissues to be the lesion is heated by the heating needle, by directly using the instrument insertion channel of ultrasonic endoscope used in the endoscopic ultrasound-guided fine needle aspiration, so it is possible to heat and treat only the cancer tissues to be the lesion at pinpoint surely.

In one embodiment of the present invention, the heating needle may be stationary placed in the cancer tissues after retracting or retreating a puncture needle inserted through the instrument insertion channel from the tip opening of the inserting section of the ultrasonic endoscope, and the heater may be controlled to be heated to a desired temperature.

In this way, it is possible to heat and treat the cancer tissues at pinpoint surely by the heating needle, after confirming a position of the cancer tissues to be the lesion when collecting a sample by the endoscopic ultrasound-guided fine needle aspiration.

In addition, in one embodiment of the present invention, the controller may comprise: a function to supply a test current for testing a conduction state to the heater; a function to confirm a length of the heater when supplying the test current; and a function to control to supply a predetermined amount of current according to a length of the heater.

In this way, it is possible to heat the heater to a desired temperature surely by supplying an appropriate amount of current according to a length of the heater.

In addition, in one embodiment of the present invention, the current and the test current supplied to the heater from the controller may be a direct current.

In this way, it is possible to inhibit a generation of a laser, a high frequency, an electromagnetic wave, or the like by heating of the heater, so it is possible to inhibit a bad influence to healthy tissues around the cancer tissues.

In addition, in one embodiment of the present invention, the controller may supply the current to the heater such that a temperature of the heater will be 45 degrees Celsius or more and 99 degrees Celsius or less.

In this way, it is possible to heat to a desired temperature necessary for killing the cancer tissues according to the lesion, so it is possible to achieve a minimally invasive cautery treatment by heating to a patient.

As explained in the above, according to the present invention, it is possible to heat and treat only cancer tissues at pinpoint more surely, by puncturing the heating needle to the cancer tissues, after confirming a position of the cancer tissues to be the lesion when collecting a sample by the endoscopic ultrasound-guided fine needle aspiration, when treating a cancer in visceral organs such as a pancreatic cancer.

DETAILED DESCRIPTION OF THE INVENTION

Hereinafter, explaining in detail about preferred embodiments of the present invention. In addition, the embodiments explained in below will not unjustly limit the content of the present invention described in claims, and it is not limited that all the structures explained in the embodiments are necessary as means for solving the problem of the present invention.

Figure 1:
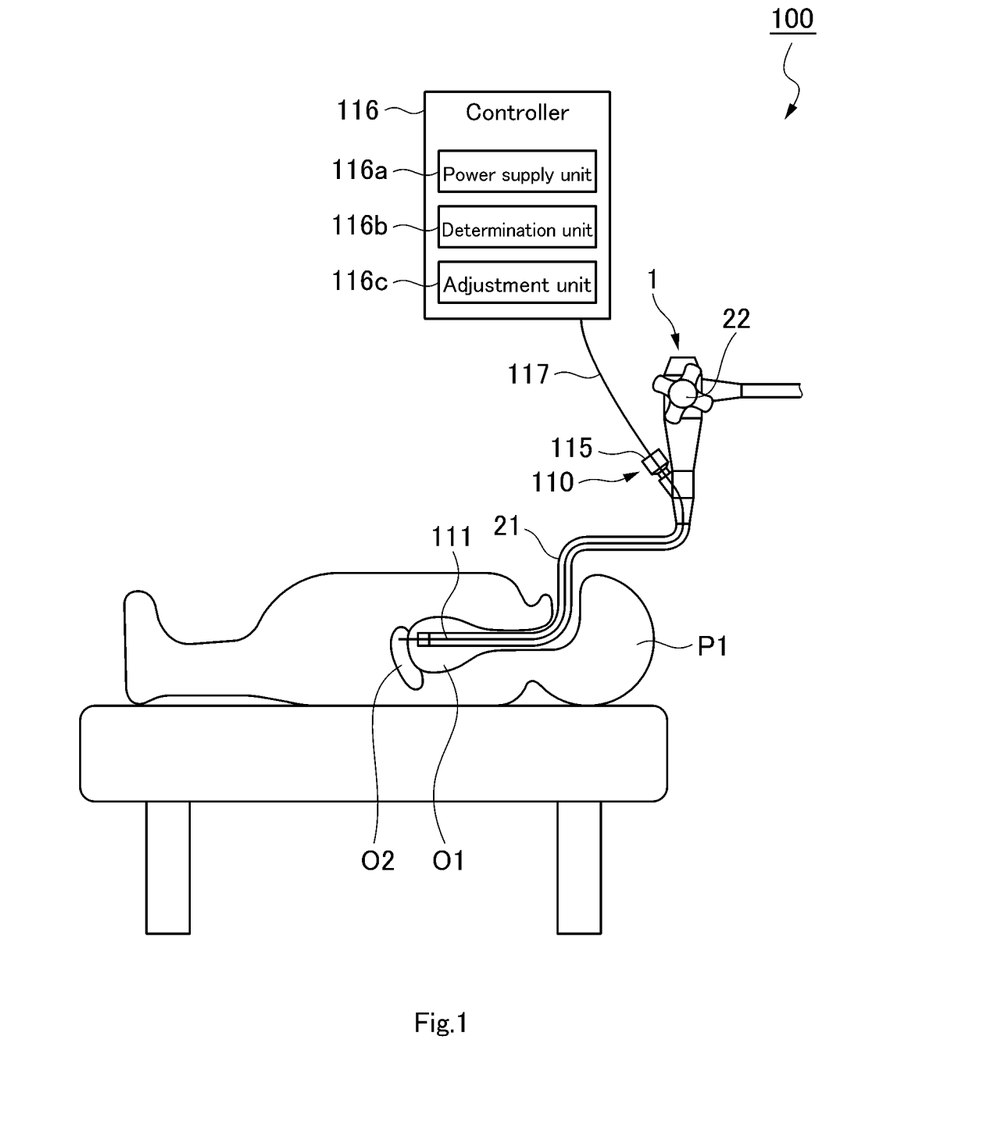
FIG. 1 is an explanatory view illustrating a schematic structure of an endoscopic cancer treatment system relating to one embodiment of the present invention.
Figure 2:
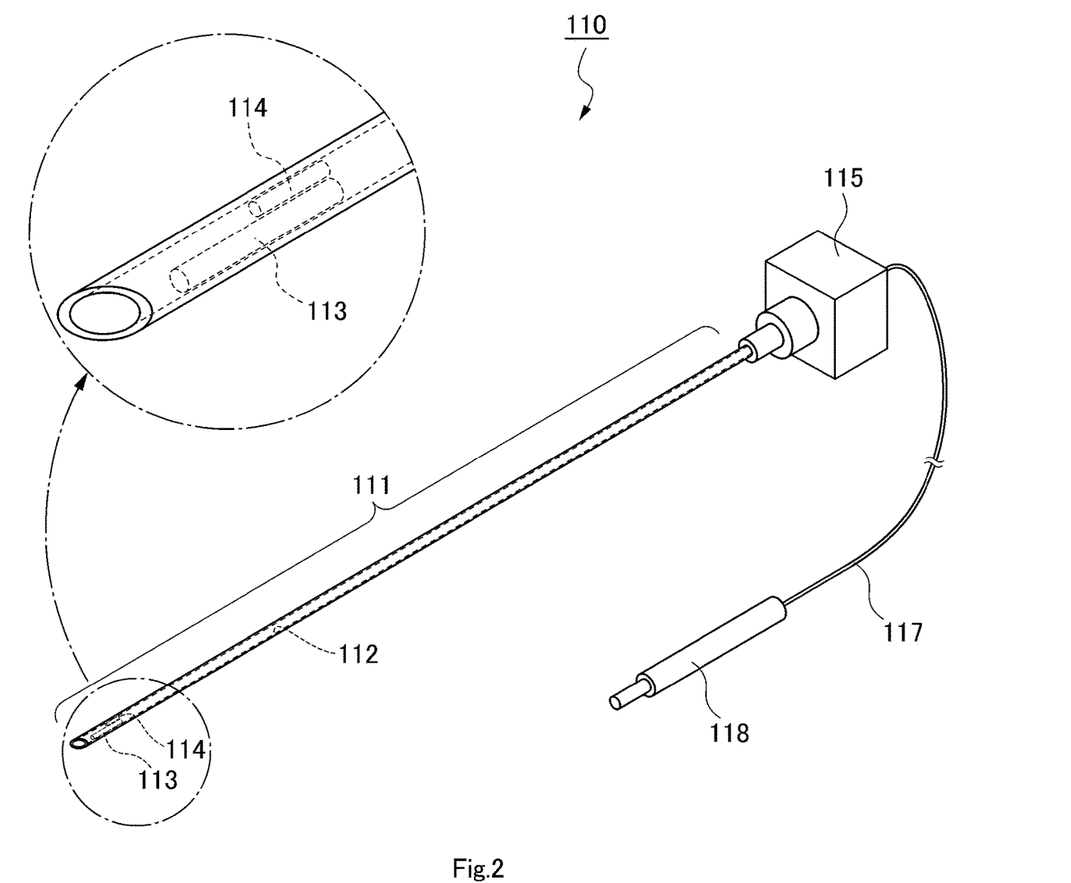
FIG. 2 is a perspective view illustrating a schematic structure of a heating needle provided in the endoscopic cancer treatment system relating to one embodiment of the present invention.

At first, explaining about a schematic structure of an endoscopic cancer treatment system relating to one embodiment of the present invention, by using the drawings. FIG. 1 is an explanatory view illustrating a schematic structure of an endoscopic cancer treatment system relating to one embodiment of the present invention, and FIG. 2 is a perspective view illustrating a schematic structure of a heating needle provided in the endoscopic cancer treatment system relating to one embodiment of the present invention.

An endoscopic cancer treatment system 100 relating to one embodiment of the present invention is a system for treating cancer tissues to be a lesion by heating by a heating needle 110 in combination with an ultrasonic endoscope 1 used in an endoscopic ultrasound-guided fine needle aspiration (EUS-FNA). Especially, the endoscopic cancer treatment system 100 of the present embodiment achieves a minimally invasive cautery treatment by heating to a patient P1, by directly heating the cancer tissues to be the lesion by the heating needle 110, by directly using a result of an approach to the lesion and an observation of the lesion by the EUS-FNA for collecting a sample from the lesion, while observing the lesion directly from inside of a body by the ultrasonic endoscope 1.

As illustrated in FIG. 1, the endoscopic cancer treatment system 100 relating to one embodiment of the present invention comprises the heating needle 110 and a controller 116. As illustrated in FIG. 2, the heating needle 110 is provided with a heater 113 and a temperature detecting element 114 at a tip side of a needle 111 to be punctured to the lesion. A part of the needle 111 is punctured to a cancered affected part such as a lung or a pancreas in a living body, so it is formed by a metal material excellent in heat conductivity and having a biocompatibility such as a stainless steel. In addition, in the present embodiment, an edge of the needle 111 of the heating needle 110 is cut such that an edge surface will be an inclined surface to be sharp, but a shape of the edge surface is not limited to this shape.

The heating needle 110 is inserted via the ultrasonic endoscope 1 from a mouth of the patient P1, so for example, an entire length of the needle 111 is about 2 m, and a diameter of the needle 111 is formed to be a thickness of about φ 0.4 mm to 1.2 mm, preferably about φ 0.45 mm. The needle 111 of this heating needle 110 is having a hollow part 112, and in the hollow part 112, the heater 113 is arranged at a needle tip side. This heater 113 is in a continuous string shape with a length of 10 to 40 mm and a thickness of 0.5 mm or less, and having a flexibility. The string-shaped heater 113 is inserted into the hollow part 112 of the needle 111 from an opening at a needle base side and arranged at a needle tip side to cauterize the affected part.

In addition, a temperature detecting element 114 such as a thermocouple or a Peltier element is arranged in the hollow part 112, other than the heater 113, to detect a temperature at a needle tip side of the needle 111, to be able to control a temperature of the needle 111 by the controller 116. For example, when a thermocouple is used as the temperature detecting element 114, the thermocouple will be arranged in the hollow part 112 by insulating with respect to the heater 113 by an insulator such as a polyimide tube. In addition, one or plurality of heaters 113 may be arranged in the hollow part 112 of the needle 111.

The heater 113 and the temperature detecting element 114 may be arranged by aligning in a longitudinal direction of the needle 111 of the heating needle 110, or may be arranged by aligning in a radial direction. When the heater 113 and the temperature detecting element 114 are arranged by aligning in a radial direction, the temperature detecting element 114 can detect a temperature on the heater 113. The temperature detecting element 114 can be protected from a heat of the heater 113 by partitioning with a heat insulating material or the like. In addition, the heater 113 may be arranged at a place other than a tip of the needle 111 of the heating needle 110, according to a purpose of treatment. At an edge of the needle 111 of the heating needle 110, the hollow part 112 is blocked by a biocompatible resin, metal or the like.

Especially, in the present embodiment, the heater 113 is configured in a string shape and having a flexibility, so a freedom of an arrangement condition of the heater 113 and the temperature detecting element 114 is increased. Therefore, by arranging the heater 113 and the temperature detecting element 114 adjacently in a longitudinal direction or in a radial direction of the needle 111 of the heating needle 110, the needle 111 with reduced diameter can be heated to a desired temperature easily, and it will be possible to heat the affected part to be an object of heating at an appropriate temperature according to a purpose of the treatment.

In the heating needle 110, a connecting code 117 connected with the heater 113 and the temperature detecting element 114 is derived from a needle base side. A plug 118 for connecting with the controller 116 is arranged at a tip of the connecting code 117. A needle base 115 provided at a base end side of the heating needle 110 is formed by a metal material in which a brass is plated with Ni or the like, or a synthetic resin material such as an electric insulating or biocompatible polymethyl pentene, polypropylene or the like. The needle base 115 is formed to be thicker than the needle 111, and composes a heating needle operating section for facilitating an operation to extract the heating needle 110 from an instrument insertion opening 25a, 25b (refer to FIG. 3) of the ultrasonic endoscope 1 by hand or by a medical equipment such as a probe, and it is blocked to prevent moisture from penetrating into the hollow part 112.

In the present embodiment, as illustrated in FIG. 1, the heating needle 110 is configured such that the needle 111 is inserted through an instrument insertion channel 31a, 31b (refer to FIG. 4) provided in an inserting section 21 of the ultrasonic endoscope 1, and that the needle 111 can be protruded or retracted from a tip opening 32a, 32b (refer to FIG. 4) provided at a tip side of the inserting section 21. And, the heating needle 110 can heat the lesion to be the affected part by puncturing the lesion via the inserting section 21 of the ultrasonic endoscope 1. Therefore, the cancer tissues to be the lesion is heated by the needle 111 of the heating needle 110 by directly using the instrument insertion channel 31a, 31b (refer to FIG. 4) of the ultrasonic endoscope 1 used in the endoscopic ultrasound-guided fine needle aspiration (EUS-FNA), so it is possible to heat and treat only the cancer tissues to be the lesion at pinpoint surely.

In addition, in the present embodiment, the heating needle 110 is configured to be able to change a length of the heater 113. Concretely, according to a size and a shape of the lesion to be the affected part, a length of the heater 113 is changed to, for example 10 mm, 20 mm, or 30 mm, so that the lesion to be an object of heating can be heated at an appropriate temperature according to a purpose of the treatment. In the present embodiment, the heating needles 110 in which a length of the heaters 113 provided at the needle 111 is different, for example 10 mm, 20 mm, 30 mm or the like, are prepared, and the heating needle 110 having the heater 113 with an appropriate length is selected accordingly, according to a size and a shape of the lesion to be the object of cauterization, and connected to the controller 116.

The controller 116 is composed by a computer or the like comprising CPU, ROM, RAM or the like, and having a function to control the heater 113 to be the predetermined temperature based on a temperature data detected by the temperature detecting element 114. In the present embodiment, as illustrated in FIG. 1, the controller 116 comprises a power supply unit 116a, a determination unit 116b, an adjustment unit 116c.

The power supply unit 116a is having a function to control a current or the like supplied to the heater 113 for heating the heater 113 to the predetermined temperature. In the present embodiment, the power supply unit 116a is having a function to supply a weak test current to the heater 113 for testing a conduction state to the heater 113, and a function to supply a current for heating the heater 113 to the predetermined temperature.

The determination unit 116b is having a function to determine a propriety of various operations when heating the heater 113 to the predetermined temperature. In the present embodiment, the determination unit 116b is having a function to determine a conduction state to the heater 113 when the test current is supplied to the heater 113, and to confirm a length of the heater 113 based on a data of a resistance value generated when supplying the test current or when a defect such as a disconnection is occurring at inside, and having a function to determine a temperature of the heater 113 based on a temperature data detected by the temperature detecting element 114.

The adjustment unit 116c is having a function to adjust a supply current to a desired amount for heating the heater 113 to the desired temperature based on a result of determination by the determination unit 116b. In the present embodiment, the adjustment unit 116c is having a function to adjust a current to a desired amount when supplying a current to the heater 13 based on a temperature data detected by the temperature detecting element 114, or when a weak test current is supplied to the heater 113. In addition, in the present embodiment, a maximum amount of current supplied to the heater 113 is 1 A, in order to secure a safety to a human body considering a risk of electric leakage or the like.

As mentioned in the above, in the present embodiment, the controller 116 is having a function to supply a weak test current to the heater 113 for testing a conduction state to the heater 113, a function to confirm a length of the heater 113 when supplying the test current to the heater 113, and a function to control to supply the predetermined amount of current to the heater 113 according to a length of the heater 113. Therefore, the heater 113 is heated to a desired temperature surely, by supplying an appropriate amount of current according to a length of the heater 113.

Especially, in the present embodiment, in order to achieve a minimally invasive cautery treatment by heating to a patient, by heating to a desired temperature necessary for killing the cancer tissues according to the lesion, the controller 116 is controlled to supply a current to the heater 113 such that a temperature of the heater 113 will be 45 degrees Celsius or more and 99 degrees Celsius or less. In other words, in the present embodiment, a treatment effect by a minimally invasive cautery treatment by heating is expected, and also, the controller 116 performs a temperature control by supplying a current to the heater 113 such that a temperature of the heater 113 will be 45 degrees Celsius or more and 99 degrees Celsius or less, as a temperature range for not occurring a local boiling.

Cancer tissues are weak to heat compared to healthy tissues, so an extremely high temperature heating is not necessary. Therefore, in the present embodiment, the heating needle 110 can kill the cancer tissues while minimizing a damage to the healthy tissues, by controlling a temperature of the heater 113 to be for example 60 degrees Celsius to apply an amount of heat to the cancer tissues in which proteins will be thermally denaturalized irreversibly.

In addition, when the temperature detecting element 114 is arranged at the needle 111 as the present embodiment, a temperature data is supplied to the controller 116 by the temperature detecting element 114, and the controller 116 controls the heater 113 such that a heating temperature will be constant. For example, even if a blood flow exists at a position where the heating needle 110 is punctured or inserted, and there is a partial loss in a temperature, a temperature of the heater 113 of respective heating needle 110 can be adjusted, so entire affected part can be heated to a desired temperature. In addition, the heater 116 may incorporate a timer, and may be controlled to turn off the heater 113 when a preset time for cauterization by heating is passed.

Further, in the present embodiment, the current and the test current supplied to the heater 113 from the controller 116 is preferably a direct current, in order to inhibit a bad influence to the healthy tissues around the cancer tissues by inhibiting a generation of a laser, a high frequency, an electromagnetic wave, or the like by heating of the heater. However, if it is in a range that a generation of a laser, a high frequency, an electromagnetic wave, or the like is inhibited when the current is supplied, a supply current such as the test current and the current may be an alternating current.

In addition, an exchange of a temperature data of the heater 113 and a control data of the heater 113 between the controller 116 and the heating needle 110 may be performed by wire as the above, or may be performed wirelessly. In addition, a power supply to the heater 113 may be supplied from the controller 116 by wire, or may be supplied from a primary battery or a secondary battery arranged at the heating needle 110.

When performing an operation using the endoscopic cancer treatment system relating to one embodiment of the present invention configured as the above, at first, a cancered lesion of a lung, a pancreas or the like in a living body to be a target of puncture is observed specifically by the ultrasonic endoscope 1, and a puncture route, a cautery temperature by heating of an affected part, a time for cauterization by heating and else are determined. Next, the heating needle 110 is connected to a medical equipment such as a probe, and a plug 118 of a connecting code 117 derived from the needle base 115 of the heating needle 110 is connected to the controller 116. Then, a needle tip is punctured or inserted to the specified affected part while confirming a depth and a direction to puncture the needle by a CT guidance, by an X-ray fluoroscopy, or a needle tip echo of an ultrasonic image of the heating needle 110.

And, by operating the controller 116, the heater 113 is heated to be the predetermined cautery temperature by heating and a needle tip portion of the heating needle 110 is heated, so the affected part is cauterized by heating for a predetermined time. At this time, the controller 116 can control the heater 113 of the heating needle 110 based on a temperature data fed back from the temperature detecting element 114. Therefore, for example, even if a blood flow exists at a position where the heating needle 110 is punctured or inserted, and there is a partial loss in a temperature, entire affected part can be heated to a desired temperature. In this way, the heating needle 110 can cauterize the affected part, only by puncturing or inserting the heating needle 110 to the affected part deeply inside a living body, so it is possible to achieve a minimally invasive cautery treatment by heating to a patient.

When the cautery treatment by heating of the affected part is completed, the treatment may be finished by just extracting the heating needle 110 from the affected part, but a pharmacotherapy, an immunotherapy or the like may be performed in combination with the cautery treatment, by supplying a medicament continuously after the cauterization by heating. In this way, by directly injecting a medicament to the affected part cauterized by heating, an effective treatment can be performed, and especially, it will be effective to a recurrence progressive cancer or the like. In addition, as a medicament to be injected, various medicaments can be used according to a treatment policy of a patient, and for example, it may be an anticancer agent or the like. In the heating needle 110 of the present embodiment, a cautery treatment to the affected part and a therapy to inject a medicament directly to the cauterized affect part can be performed continuously, so it is possible to achieve a minimally invasive treatment to a patient.

In this way, in the endoscopic cancer treatment system 100 relating to one embodiment of the present invention, the heating needle 110 incorporating the heater 113 is punctured or inserted to a living body until it reaches the affected part, and then, the heater 113 is heated to a predetermined temperature, and the affected part is cauterized by heating. Therefore, a minimally invasive treatment can be achieved without an abdominal operation or the like, as it can be performed only by puncturing or inserting the heating needle 110 to reach the affected part. In addition, there is no risk of a radiation exposure like a radiation therapy, and the patient does not feel a pain or a numbness as a radio frequency treatment, and also, the surrounding tissues will not be damaged.

In addition, a temperature data will be fed back to the controller 116 by incorporating the temperature detecting element 114 in the heating needle 110, so a temperature control of the heater 113 can be performed more finely. Especially, in the endoscopic cancer treatment system 100 relating to the present embodiment, when treating a cancer in visceral organs such as a pancreatic cancer, the heating needle is punctured to the cancer tissues after confirming a position of the cancer tissues to be the lesion when collecting a sample by the endoscopic ultrasound-guided fine needle aspiration, so it is possible to heat and treat only the cancer tissues at pinpoint more surely. In addition, the endoscopic cancer treatment system 100 relating to one embodiment of the present invention can be used to various cancer treatments, other than the above-mentioned pancreatic cancer and lung cancer, such as a uterine cancer and a kidney cancer. In addition, it can be used to a heating treatment of an affected part of an animal other than a human such as a companion animal, for example a dog and a cat.

Figure 3:
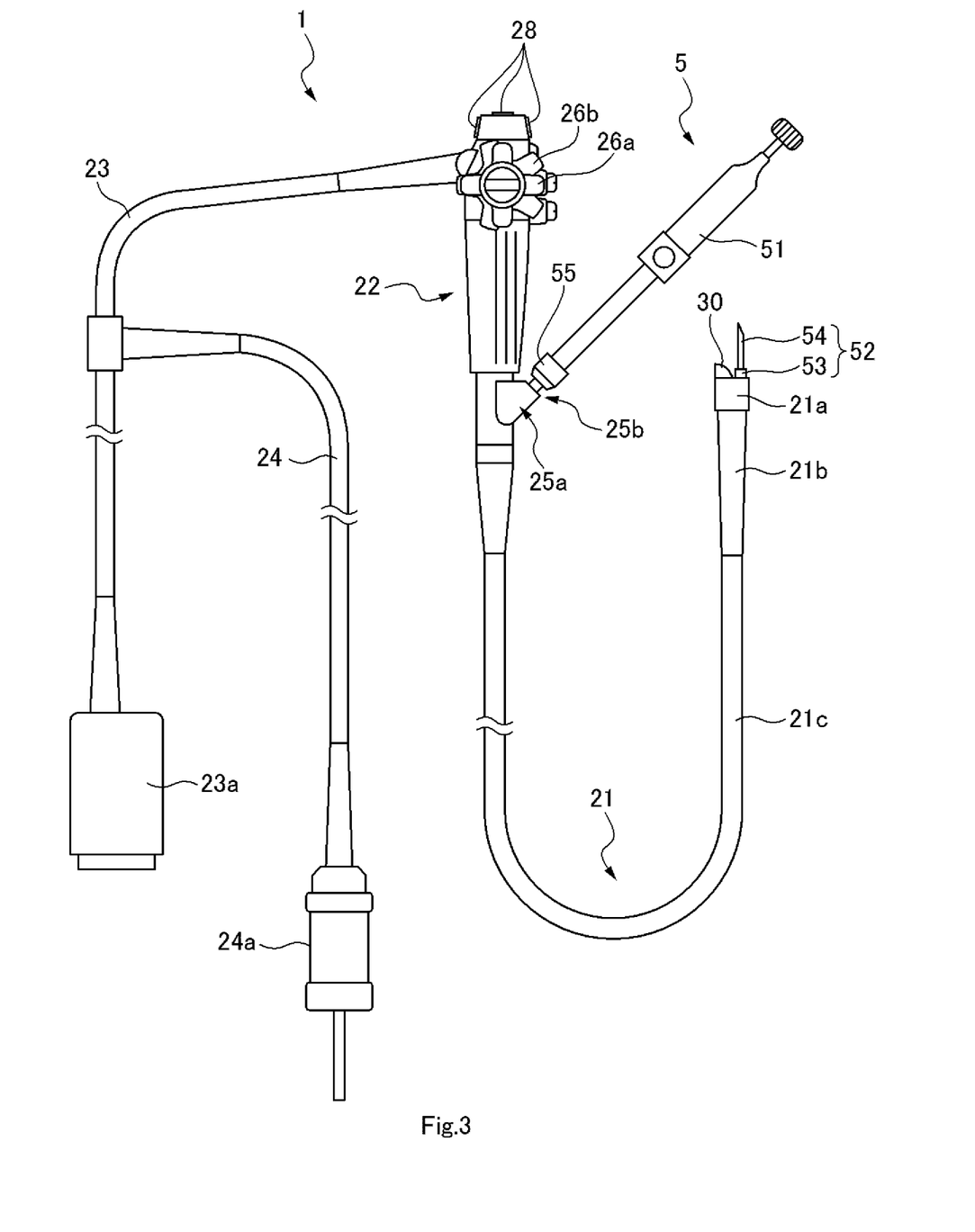
FIG. 3 is an explanatory view illustrating a schematic structure of an ultrasonic endoscope used in the endoscopic cancer treatment system relating to one embodiment of the present invention.
Figure 4:
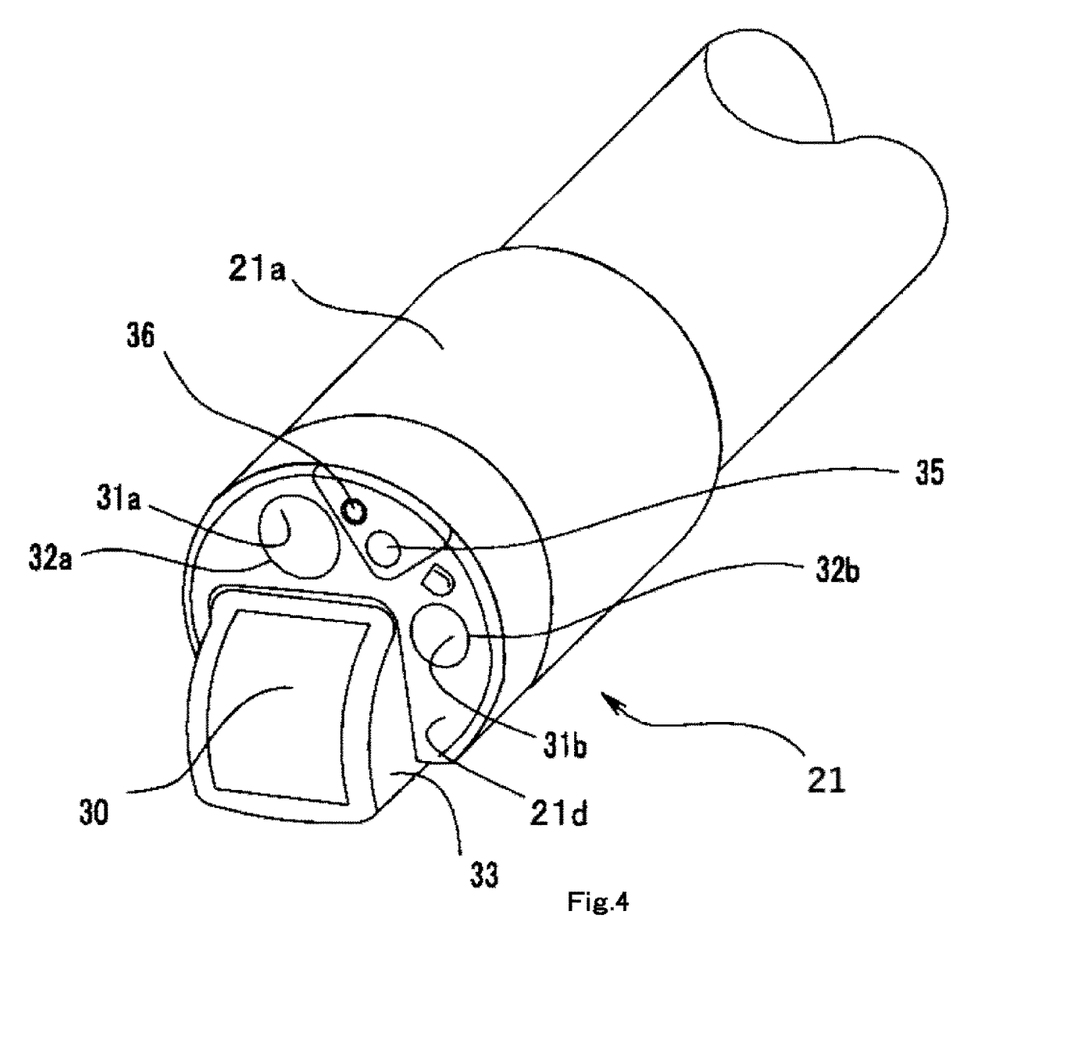
FIG. 4 is a schematic perspective view illustrating a tip of the ultrasonic endoscope used in the endoscopic cancer treatment system relating to one embodiment of the present invention.
Figure 5:
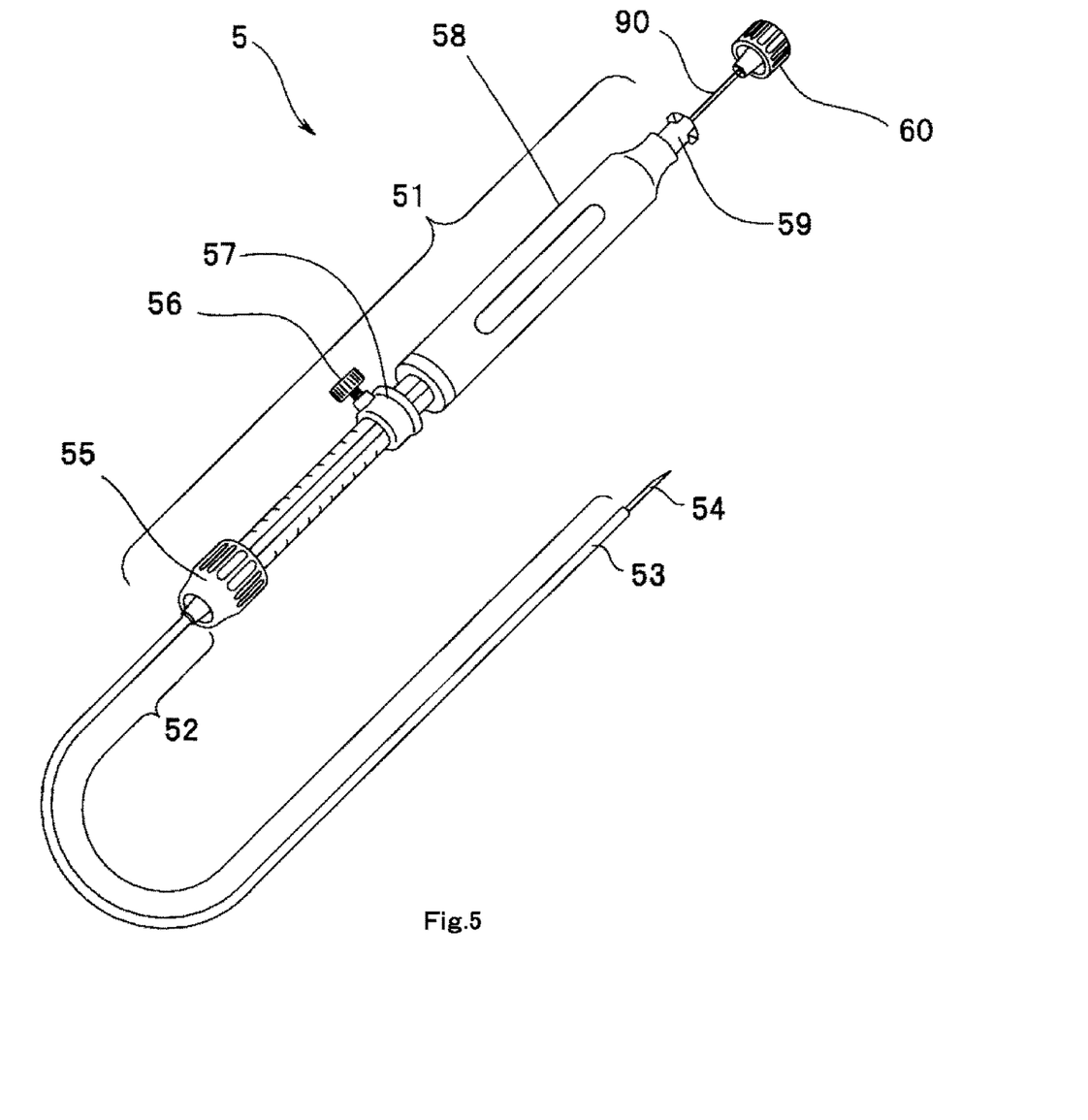
FIG. 5 is a perspective view illustrating a structure of a puncture needle in the ultrasonic endoscope of FIG. 3.
Figure 6:
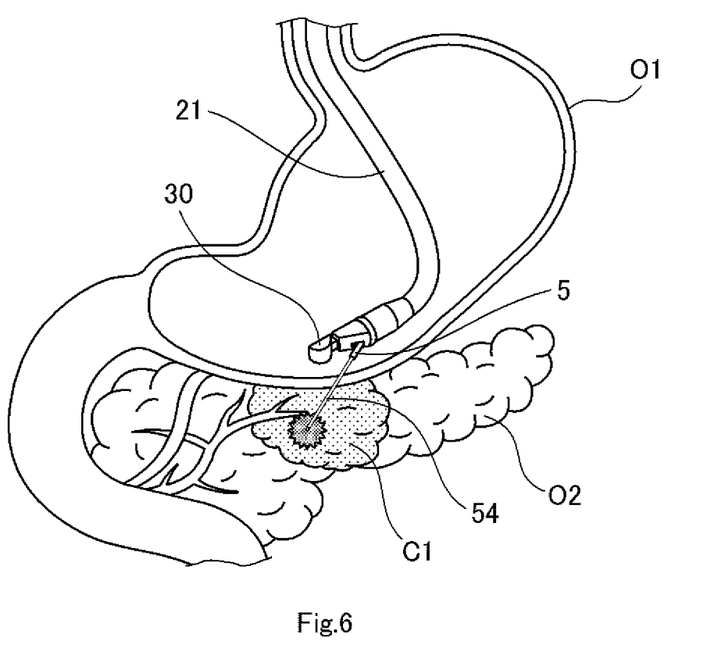
FIG. 6 is an explanatory view of an operation for collecting a sample by an endoscopic ultrasound-guided fine needle aspiration performed via the ultrasonic endoscope used in the endoscopic cancer treatment system relating to one embodiment of the present invention.

Next, explaining about an ultrasonic endoscope used in the endoscopic cancer treatment system 100 relating to one embodiment of the present invention, by using the drawings. FIG. 3 is an explanatory view illustrating a schematic structure of an ultrasonic endoscope used in the endoscopic cancer treatment system relating to one embodiment of the present invention, FIG. 4 is a schematic perspective view illustrating a tip of the ultrasonic endoscope used in the endoscopic cancer treatment system relating to one embodiment of the present invention, and FIG. 5 is a perspective view illustrating a structure of a puncture needle in the ultrasonic endoscope of FIG. 3. In addition, FIG. 6 is an explanatory view of an operation for collecting a sample by an endoscopic ultrasound-guided fine needle aspiration performed via the ultrasonic endoscope used in the endoscopic cancer treatment system relating to one embodiment of the present invention.

As illustrated in FIG. 3, an ultrasonic endoscope 1 used in the endoscopic cancer treatment system 100 relating to one embodiment of the present invention comprises: an inserting section 21 to be inserted into a body; an operating section 22 located at a base end of the inserting section 21; a universal code 23 extending from a side of the operating section 22; and a cable 24 for a light source separated at a middle of the universal code 23. And in the ultrasonic endoscope 1, when collecting a sample by the endoscopic ultrasound-guided fine needle aspiration, a puncture needle 5 is inserted from an instrument insertion opening 25a, 25b (the instrument insertion opening 25b is omitted in the drawing) provided at a tip side of the operating section 22, and a collection of a sample of the lesion is performed by the puncture needle 5.

In the inserting section 21, a hard tip 21a, a curved part 21b, and a flexible tube 21c are connected in order from a tip side. The curved part 21b is configured to be bent actively in up down and left right directions, for example by an operation of curve operating knobs 26a, 26b of the operating section 22. The flexible tube 21c is having a flexibility.

At a base end of the universal code 23, an ultrasonic connector 23a capable of mounting to and removing from unillustrated ultrasonic observation device is provided. At a base end of the cable 24 for the light source, an endoscope connector 24a capable of mounting to and removing from unillustrated light source device or video processor device is provided.

At a tip side of the operating section 22, instrument insertion openings 25a, 25b (the instrument insertion opening 25b is omitted in the drawing) are provided. The instrument insertion openings 25a, 25b respectively communicate with instrument insertion channels 31a, 31b (refer to FIG. 4) provided in the inserting section 21. The instrument insertion opening 25a comprises a cap, and a fixed ring 55 provided at a handle 51 of the puncture needle 5 or the like will be connected to the cap. The fixed ring 55 is capable of mounting to and removing from the cap. And, a needle tube 54 of the puncture needle 5 is inserted through the instrument insertion channel 31a via the instrument insertion opening 25a. In addition, other instrument such as the heating needle 110, an ultrasonic probe or the like is inserted through the instrument insertion channel 31b via the instrument insertion opening 25b.

As illustrated in FIG. 4, the instrument insertion channels 31a, 31b respectively comprise tip openings 32a, 32b in a tip surface 21d of the hard tip 21a. A central axis near the tip opening 32s of the instrument insertion channel 31a is arranged to be almost coincide with an ultrasonic scanning surface by an ultrasonic oscillator 30, and an instrument for performing a treatment such as a puncture can be inserted through the instrument insertion channel 31a. In addition, an objective optical system 35 and an illumination optical system 36 are arranged at a tip surface 21d of the hard tip 21a.

An electronic scanning ultrasonic oscillator 30 is arranged at a tip side of the hard tip 21a. The ultrasonic oscillator 30 is, for example a convex array, and configured by aligning a plurality of ultrasonic elements inside thereof. The ultrasonic endoscope 1 can obtain an echo signal by transmitting and receiving an ultrasonic wave by the ultrasonic oscillator 30 while switching each ultrasonic element. The echo signal from the ultrasonic oscillator 30 is transmitted to unillustrated ultrasonic observation device via an ultrasonic connector 23a. And, an ultrasonic image (linear image) having a cross section parallel to an insertion axis of the inserting section 21 can be obtained based on the echo signal from the ultrasonic oscillator 30.

In the present embodiment, a structure to protrude relatively largely from the tip surface 21d is not arranged in between the tip openings 32a, 32b. Therefore, when the puncture needle 5 is inserted through the instrument insertion channel 31a to protrude the needle tube 54 from the tip opening 32a, and when other instrument such as the ultrasonic probe or the like is inserted through the instrument insertion channel 31b to protrude the ultrasonic oscillator provided at a tip of the ultrasonic probe from the tip opening 32b, the needle tube 54 can be depicted by the ultrasonic probe. In addition, in the present embodiment, two instrument insertion channels 31a, 31b and two tip openings 32a, 32b are respectively arranged at the inserting section 21 of the ultrasonic endoscope 1, but a number of these members are not limited to two, and it may be one or three or more.

In addition, in the present embodiment, the ultrasonic oscillator 30 comprises a protruding section 33 protruding from the hard tip 21a. The protruding section 33 is arranged at a position other than on a line linearly connecting between the tip openings 32a, 32b. In addition, an ultrasonic reflection machining may be performed on a surface of the protruding section 33, in order to facilitate an ultrasonic observation of the protruding section 33. As the ultrasonic reflection machining, for example, a concavo-convex processing such as a sandblast process, a satin finished process, and a dimple forming process, or a coating processing of a resin containing an air bubble or a metal powder can be considered.

As illustrated in FIG. 5, the puncture needle 5 is configured to comprise a handle 51 and a channel inserting section 52, and the channel inserting section 52 is configured to comprise a sheath 53 and the needle tube 54. The channel inserting section 52 is configured to be inserted through the instrument insertion channel 31a from the instrument insertion opening 25a, and to be able to protrude from the tip opening 32a (refer to FIG. 4).

The handle 51 is configured to arrange, for example a fixed ring 55, an adjuster knob 56, a needle adjuster 57, a needle slider 58, an inlet cap 59 and a stylet cap 60 in order from a tip side. The needle tube 54 is arranged to be inserted through the sheath 53 to be freely movable with respect to the sheath 53. This needle tube 54 is formed by a metal pipe, for example a stainless-steel pipe or a nickel-titanium pipe. A sharp shaped edge is formed at a tip of the needle tube 54.

The stylet cap 60 is connected with the inlet cap 59 by connecting a stylet 90 or a stylet 90a to be inserted into the needle tube 54 to the stylet cap 60. A base end of the needle tube 54 is fixed integrally to the inlet cap 59 by bonding or the like. The needle adjuster 57 is slidably fixed or released by the adjuster knob 56. The needle slider 58 will be able to slide by releasing a fixation of the needle adjuster 57 by loosening the adjuster knob 56. In addition, a protruding length of the needle tube 54 from a tip of the sheath 53 can be adjusted by adjusting a distance between fixed positions of the needle slider 58 and the needle adjuster 57 accordingly.

By using such ultrasonic endoscope 1 and the puncture needle 5, a collection of a sample by the endoscopic ultrasound-guided fine needle aspiration is performed. Concretely, as illustrated in FIG. 6, in the endoscopic ultrasound-guided fine needle aspiration, with respect to a digestive tract or the like such as a pancreas O2, in which a biopsy by a percutaneous puncture or a normal endoscopic biopsy is difficult, an ultrasonic wave is emitted from the ultrasonic oscillator 30 provided at a tip side of the inserting section 21 to observe a pancreas O2 via a stomach O1. And, in order to definitely diagnose a cancerization of a lesion C1 of a pancreas O2, the needle tube 54 is punctured toward the lesion C1 of a pancreas O2 from inside of a stomach O1, and cancer cells or tissues of the lesion C1 are sampled by aspiration by the needle tube 54.

Figure 7A:
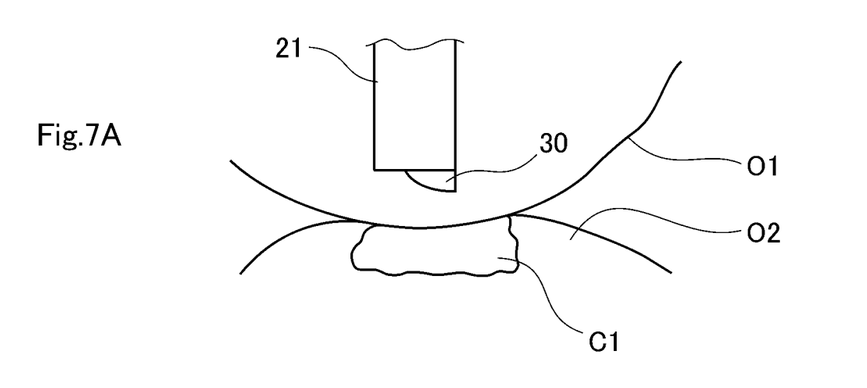
FIG. 7A to FIG. 7C are explanatory views of an operation of a cancer treatment by the endoscopic cancer treatment system relating to one embodiment of the present invention.
Figure 7B:
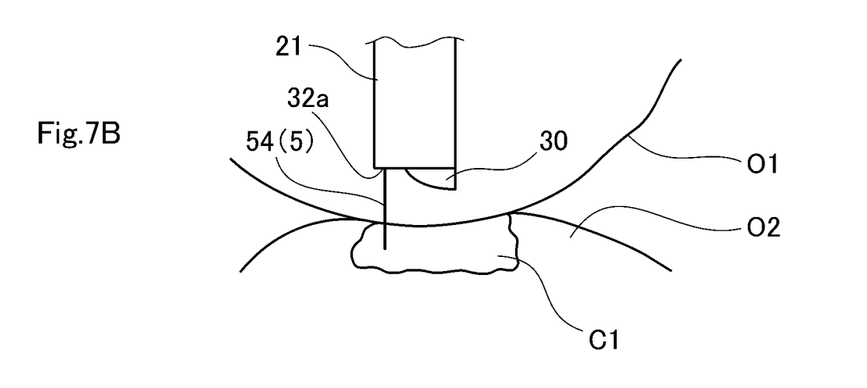
Figure 7C:
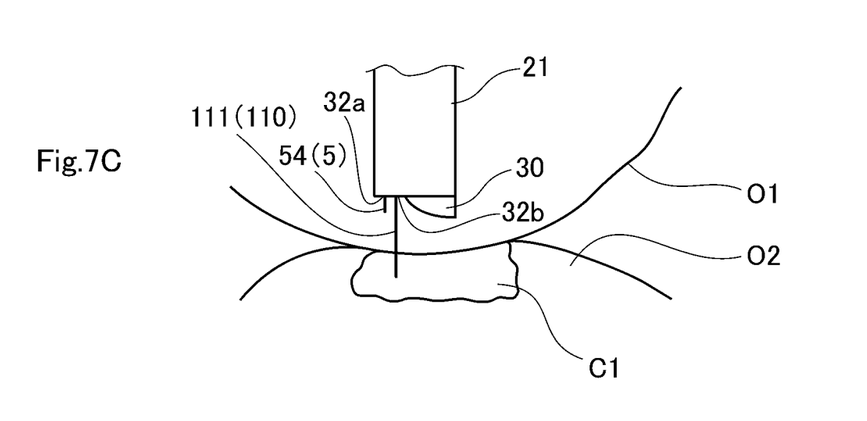

Next, explaining about an operation of a cancer treatment by the endoscopic cancer treatment system relating to one embodiment of the present invention, by using the drawings. FIG. 7A to FIG. 7C are explanatory views of an operation of a cancer treatment by the endoscopic cancer treatment system relating to one embodiment of the present invention.

In the endoscopic cancer treatment system 100 relating to one embodiment of the present invention, the heating needle 110 is stationarily placed in the cancer tissues of the lesion, where the sample is collected, to be able to cauterize only the cancer tissues surely, by using the ultrasonic endoscope used when collecting a sample by the endoscopic ultrasound-guided fine needle aspiration.

Concretely, as illustrated in FIG. 7(A), an ultrasonic wave is emitted from the ultrasonic oscillator 30 provided at a tip side of the inserting section 21 of the ultrasonic endoscope 1 (refer to FIG. 1) to observe a pancreas O2 via a stomach O1. And, as illustrated in FIG. 7(B), when a lesion C1 being suspected of a cancer is found in a pancreas O2, the needle tube 54 of the puncture needle 5 is protruded from the tip opening 32a provided at a tip side of the inserting section 21, and then, the needle tube 54 is punctured toward tissues being suspected of a cancer in the lesion C1 of a pancreas O2 from inside of a stomach O1. And, the needle tube 54 collects cancer cells or tissues of the lesion C1 by aspiration.

When the tissues collected by aspiration is definitely diagnosed as malignant (cancer), as illustrated in FIG. 7(B), the needle tube 54 of the puncture needle 5 is punctured to the lesion C1 again in a same manner in another day, and the needle 111 of the heating needle 110 is inserted into the needle tube 54, and after confirming that the needle 111 has reached to the lesion C1, the needle tube 54 is retreated and the needle 111 of the heating needle 110 is stationarily placed at the lesion C1, and the heater 113 of the heating needle 110 may be controlled to be heated to a desired temperature.

In addition, as illustrated in FIG. 7(C), after the needle tube 54 of the puncture needle 5 inserted through the instrument insertion channel 31a (refer to FIG. 4) and protruding from the tip opening 32a of the inserting section 21 of the ultrasonic endoscope 1 is retreated, the needle 111 of the heating needle 110 inserted through another instrument insertion channel 31b (refer to FIG. 4) and protruding from another tip opening 32b of the inserting section 21 is punctured to the lesion C1, and the heater 113 of the heating needle 110 may be controlled to be heated to a desired temperature.

In this way, the endoscopic cancer treatment system 100 relating to the present embodiment can heat and treat the cancer tissues by the needle 111 of the heating needle 110 at pinpoint by the heater 113 with desired length and temperature, after confirming a size and a position of the cancer tissues to be the lesion C1, when collecting a sample by the endoscopic ultrasound-guided fine needle aspiration.

As explained in the above, by applying the endoscopic cancer treatment system relating to one embodiment of the present invention, when treating a cancer of organs such as a pancreatic cancer, it will be possible to insert the heating needle toward the cancer tissues, after confirming a size and a position of the cancer tissues to be the lesion, when collecting a sample by the endoscopic ultrasound-guided fine needle aspiration. In this way, the heating needle having the heater with more appropriate length can be selected with respect to the cancer tissues, and the heater can be heated to a desired temperature, after confirming a size and a position of the cancer tissues to be the lesion. Therefore, it is possible to heat and treat only the cancer tissues to be the lesion at pinpoint more surely, so it is possible to achieve a minimally invasive cautery treatment by heating to a patient.

In addition, by applying the endoscopic cancer treatment system relating to one embodiment of the present invention, it will be possible to heat and treat the cancer tissues to be the lesion at pinpoint surely by a suitable temperature by using the heating needle, after confirming a size and a position of the cancer tissues to be the lesion, when collecting a sample by the endoscopic ultrasound-guided fine needle aspiration, with respect to a digestive tract or the like such as a pancreas O2, in which a biopsy by a percutaneous puncture or a normal endoscopic biopsy is difficult. Especially, different from other organs such as a liver, a pancreas does not have a regenerating function in cell tissues composing the organ, so it is necessary to avoid a damage by unnecessary excessive heat. Therefore, the endoscopic cancer treatment system relating to the present embodiment can heat and treat only the cancer tissues to be the lesion at pinpoint surely by a necessary temperature more surely, so it can be applied suitably as the endoscopic pancreatic cancer treatment system, and it is having an extremely significant industrial value.

In addition, it is explained in detail about each embodiment and each example of the present invention as the above, but it can be understood easily for those who skilled in the art that various modifications can be made without practically departing from new matters and effect of the present invention. Therefore, all such variants should be included in the scope of the present invention.

For example, terms described with different terms having broader or equivalent meaning at least once in description and drawings can be replaced with these different terms in any part of description and drawings. In addition, operation and configuration of the endoscopic cancer treatment system are not limited to those explained in each embodiment and each example of the present invention, and various modifications can be made.

Glossary of Drawing References

1 Ultrasonic endoscope
5 Puncture needle
21 Inserting section
22 Operating section
31a, 31b Instrument insertion channel
32a, 32b Tip opening
100 Endoscopic cancer treatment system
110 Heating needle
111 Needle
112 Hollow part
113 Heater
114 Temperature detecting element
115 Needle base
116 Controller
116a Power supply unit
116b Determination unit
116c Adjustment unit
117 Connecting code
118 Plug

The invention claimed is:

1. An endoscopic cancer treatment system for heating and treating cancer tissues to be a lesion, comprising:
    an ultrasonic endoscope used in an endoscopic ultrasound-guided fine needle aspiration and comprising an inserting section to be inserted into a body, wherein two instrument insertion channels are arranged at the inserting section, the two instrument insertion channels respectively comprising a tip opening at a tip side of the insertion section;
    a puncture needle for confirming the lesion wherein the puncture needle is inserted through the instrument insertion channel from the opening of the inserting section of the ultrasound endoscope;
    a heating needle provided with a heater to heat the heating needle and a temperature detecting element at a tip side; and
    a controller for controlling the heater to a predetermined temperature based on a temperature data detected by the temperature detecting element,
    wherein the heating needle is configured to be inserted through an instrument insertion channel of the two instrument insertion channels to be able to protrude or retract from the tip opening provided at the tip side of the inserting section, and
    the controller comprises:

a power supply unit for supplying a test current for testing a conduction state to the heater;

a determination unit for confirming a length of the heater when supplying the test current; and an adjustment unit for controlling to supply a predetermined amount of current according to a length of the heater, wherein the heating needle is stationary placed in the cancer tissues to heat the tissues after retracting or retreating the puncture needle inserted through the instrument insertion channel from the tip opening of the inserting section of the ultrasonic endoscope, and the heater is controlled to be heated to a desired temperature.

2. The endoscopic cancer treatment system according to claim 1, wherein the current and the test current supplied to the heater from the controller is a direct current.

3. The endoscopic cancer treatment system according to claim 1, wherein the controller supplies the current to the heater such that a temperature of the heater will be 45 degrees Celsius or more and 99 degrees Celsius or less.

* * * * *